United States Patent [19]

Grahn et al.

[11] Patent Number: 4,964,302

[45] Date of Patent: Oct. 23, 1990

[54] TACTILE SENSOR

[76] Inventors: Allen R. Grahn, 3735 Emigration Canyon, Salt Lake City, Utah 84018; Lynn Astle, 4291 Holly Drive, Salt Lake City, Utah 84124

[21] Appl. No.: 653,904

[22] Filed: Sep. 25, 1984

[51] Int. Cl.$^5$ .............................................. G01B 17/02
[52] U.S. Cl. .................. 73/865.7; 73/862.04; 73/628; 310/800; 901/46
[58] Field of Search .......... 73/DIG. 4, 862.04, 862.64, 73/432 T, 62, 628, 629, 703; 310/338, 800; 901/33, 46; 33/125 W

[56] References Cited

U.S. PATENT DOCUMENTS 3,969,960 7/1976 Pagano ................................... 73/761
4,473,769 9/1984 Ngyuen ........................... 310/800 X

FOREIGN PATENT DOCUMENTS 2757099 6/1978 Fed. Rep. of Germany ...... 310/800
0643322 1/1979 U.S.S.R. ................................ 901/46

Primary Examiner—Charles A. Ruehl

[57] ABSTRACT

A sensor comprising a deformable medium, such as rubber, an ultrasonic transducer for transmitting a signal through the medium to a face of the medium and for sensing an echo of the signal returned from the face through the material to the transducer and circuit means for determining the time differential between transmission of the signal and return of the echo and for converting the time signal into a distance measurement.

9 Claims, 1 Drawing Sheet

TACTILE SENSOR

BACKGROUND OF THE INVENTION

1. Field of the Invention

This invention relates to sensing devices. It is particularly concerned with tactile sensors that can detect touch and detect and quantitate applied and reactive forces and applied force components normal to the sensor surface and the distribution of those forces on the sensor surface. Principal uses of such sensors are in robotics, teleoperation, industrial automation and prosthetics.

2. Prior Art

There has been a great deal of development effort in the past with regard to apparatus and devices, such as industrial robots and sub-systems for use with them, that will accomplish desired work objects. The field of industrial robots, for example, has expanded rapidly but further progress is presently limited by the absence of low cost adequate sensor perception and feedback control systems. Technology presently exists to permit design of robots able to respond to control signals and to move even as little as a few thousandths of an inch to accomplish their designed tasks. Such robots are usually engineered to accomplish specific jobs in well-defined work environments, and they are usually complex and costly.

A great deal of emphasis has previously been placed on artificial vision systems that will serve as "eyes" for a robot in the detection of objects or circumstances and that will provide signals for responsive operation of the robot. Consequently, the artificial vision systems have become quite sophisticated, while tactile sensors that have not received the same design emphasis have generally remained rather crude, often having coarse spatial resolution and slow response times.

Tactile sensors can synergistically complement visual systems by becoming the controlling system at the time contact is made between a gripper of the robot and an object or objects being gripped, this being a time when vision is often obscured. The potential importance of tactile information is evident when it is realized that the information can readily operate a robot hand to function in a manner comparable to the way a blindfolded person can sense objects and perform simple functions such as the threading of a nut onto a bolt.

It is believed that continuing advances in industrial robotics will require robots capable of performing tasks that will place a premium on the tactile sensory perception capability of the machines. It is also believed that relatively low cost touch responsive sensors are required for use with such robots. A number of motion control and force sensor devices have been heretofore disclosed. Representative of these devices are those shown in U.S. Pat. Nos. 3,307,393; 3,416,365; 4,098,001; 4,155,169; 4,156,835; and 4,094,192. These known devices may be useful for their specific design purposes and they are generally designed for use in complex mechanical systems, with the chief objective of the systems being to obtain high precision. However, because in most circumstances sensory feedback is lacking, the degree of precision obtained is not as high as desired.

Other force sensors have been developed, and when such individual force sensing elements are placed in an array, force distribution or tactile sensing can be achieved. One such design uses a sandwich structure of two linear arrays of electrodes separated by a thin material, the electrical conductivity of which changes with pressure. By constructing the array in such a manner that the two arrays of electrodes intersect diagonally, a force-sensitive cell is defined at the intersection. The dimensions of the cell are defined by the width and separation of the electrodes.

Another force sensor concept employs small "windows" that are arranged in a matrix. The "windows" are electrodes that are surrounded by a common grounding medium. When a conducting material covering the electrodes is deflected with sufficient force current will flow from the electrodes to the grounded material.

Still another variation of a force-sensor array consists of utilizing a sheet of silicone rubber and an etched circuit board. The rubber sheet is made of alternating conducting and nonconducting layers with the conducting layers being silver or graphite impregnated rubber. The conducting layers of the rubber sheet are placed in a perpendicular relationship to circuit board conductors. The contact points at each intersection then form pressure sensors. Complex data output and readout circuitry are required to obtain and use this force-sensor array.

Other devices utilize conducting rubber in association with a semiconductor material. The limitations of these devices center around the potential contamination of the semiconductor material as well as abrasion of the rubber surface. In addition, as with other devices utilizing conducting rubber, the response indicated between the deformation of the rubber and the pressure applied is often non-linear. In linearizing the response of the rubber, means are provided to digitize the pressure response. One method of linearizing employs a triangle-shaped device with a series of electrodes along two sides of the triangle. Progressively larger forces applied to a rubber surface resting on a corner of the triangle will cause the corner to penetrate into the rubber and to contact an increasing number of electrodes as the penetration continues and increases.

An optical device, made by the Lord Corporation of North Carolina, U.S.A. employs a small force-sensing device consisting of a small shutter that controls a light beam in conjunction with a light emitting diode and photodetector. Each element requires individual calibration.

While the prior art devices discussed above may each be suitable for a specific use for which it is designed, they are not widely adaptable for use because of their expense, complexity, nonlinear readouts and/or limited performance when used generally. It has been found, however, that an ultrasonic distance measuring device which measures the thickness of a compressible medium meets the general requirements necessary to provide a tactile sensor suitable for a wide range of uses. If a resilient medium is used, the device is adaptable for repeated uses.

The use of sound in the measuring of distance has long been known. In many applications ultrasonic pulse echoes or mechanical vibrations, are used for precision measurement of various properties of a given piece of material. Attention is directed to U.S. Pat. Nos. 4,033,244; 3,994,154; 3,688,565; 3,228,232; 3,108,469; 3,745,833; 4,044,606; 3,315,520; 3,540,265; 3,416,365; and 3,942,381. As illustrated in these patents both thickness and acoustic properties of the material can be measured.

SUMMARY OF THE INVENTION

The present invention comprises a sensor which detects contact and/or measures forces occurring between the sensor and an object. An ultrasonic pulse generated by a transducer travels through a medium, is reflected from a surface of the medium, returns through the medium, and is detected at the transducer. If the material at the other side of the interface with the medium has a lower acoustic impedance than does the medium itself, such as occurs when air is present at the reflecting surface, versus, for example, a rubber medium, the echo is inverted, i.e., undergoes a 180° phase shift upon reflection. If, however, the medium is in contact with an object having a greater acoustic impedance the echo will be reflected, but will not undergo a 180° phase shift. Consequently, the ultrasonic pulse is reflected whether or not an object is in contact with the sensor medium.

Since whether the signal is inverted or not depends upon whether a contacted object has a greater acoustic impedance than the rubber, this characteristic can be used in identifying the nature of the object. However, if the material contacting the surface has an acoustic impedance similar to the rubber, then the sound will be poorly reflected unless an acoustic "mirror" is incorporated into the interface by use of a medium having a different acoustic impedance. This can be done, for example, by building in an air gap or a metal layer at the interface.

Since it is possible to calculate the speed of travel of an ultrasonic pulse through a medium or composite media and since the pulse will be reflected by an interface, the thickness of the medium or media can be determined by measuring the two-way travel time of generated pulses.

Forces applied to the surface of the sensor by an object can be calculated from the measurement of the deformation of the medium by the object with knowledge of the force necessary to deform the medium a known amount.

The composition and configuration of the medium may take on many forms for different applications. For example, it may be an elastomeric pad used on the fingers of a robot gripper; it may be a device where the sensor measures movement of a spring-loaded rigid plate through an intermediate medium such as air, fluids or gels; or a nonresilient medium might be used to measure the maximum force applied.

It has been found that for transducers used in sensors of the invention, certain characteristics are deemed desirable: First, the transducer must operate at a high enough frequency to provide good distance resolution, to simplify detection and to avoid interference between a transmitted pulse and the returning echo of the pulse within very short distances that are involved. Second, the transducer and associated apparatus preferably will be small and light enough not to make the sensor too large for use with other structures. Third, the transducers ideally are adaptable for use in compact arrays. To achieve these characteristics a small, high frequency transducer must be used. While other transducers can be used, it has been found that polyvinylidene fluoride (PVDF), a thin film polymer exhibiting excellent piezoelectric characteristics, has been found desirable as a transducer material. PVDF is inexpensive, rugged and flexible and can be molded to fit various surfaces. It is thin enough to not add significantly to the bulk of a sensor array and has a high dampening factor to avoid ringing in generating the transmission pulse and receiving the echo pulse. In addition, the acoustic impedance of PVDF is relatively close to that of rubber and to some epoxy adhesives allowing strong coupling of the ultrasonic pulse into these materials. Also, PVDF has low acoustic cross-coupling through the material, which provides acoustic isolation of array elements. Finally PVDF can be used in conjunction with photo-reduction and photo-lithographic techniques for mass production of array or electrode patterns. While PVDF has low efficiency as an ultrasound transmitter and a limited upper operating temperature, these characteristics are not severe limitations for the device. In the event that PVDF material is not satisfactory for a particular sensor, other transducers, for example, such as those made of quartz, lead titanate-zirconate or other ceramic or piezo-electric polymers can be used.

OBJECTS OF THE INVENTION

A principal object of the present invention is to provide a sensor that is adaptable to a wide range of uses in sensing devices.

Another object is to provide a device that is capable of sensing contact with great sensitivity.

Yet another object of the present invention is to provide a sensing device that is capable of accurately determining shape by good spatial resolution of force distributions.

Still another object of the present invention is to provide a measuring device capable of sensing force with suitable precision and sensitivity.

Another principal object of the present invention is to provide a force measuring device that is capable of sensing the distribution of force applied to a given surface.

FEATURES OF THE INVENTION

Principal features of the invention include one or more ultrasonic transducers arranged to generate pulses into a suitable deformable medium. In the presently preferred embodiment, an ultrasonic transducer generates pulses into an elastic pad made of a compressible substance such as rubber. Each transducer generates a signal used to measure a change in the thickness of the elastic pad, which is representative of the force applied to the pad in the vicinity of the transducer. With the transducers arranged in either a one or a two-dimensional array, and electronically connected to appropriate circuitry, direct and reactionary forces applied to the overall surface area of the pad can be measured and the sensor can detect the force distribution. It is then possible to determine the shape of an object coming in contact with the pad surface overlying the array. Conventional pulse-echo, time-of-flight measuring circuitry or conventional phase-shift circuitry can be used with the sensor of the invention to signal contact of a sensor with an object and to provide signals indicative of a plurality of contacts that will provide information regarding shape of an object being contacted.

While many types of deformable media may be used, natural, synthetic and silicone rubbers may be found highly satisfactory for the purposes of the invention.

In one preferred embodiment of the invention, a plurality of transducers is covered by a single sheet of deformable material. In an alternate embodiment of the invention, each transducer used has its individual deformable pad. The choice between the alternative embodiments is based on economics and the specific sensing requirements involved. In either of the alternative embodiments, the array itself can be flat or may be shaped, i.e., curved, to match the shape of a particular object being handled. Since the sensor of the invention, in addition to sensing contact, effectively measures shape and force distribution, it also measures changes in force distribution caused by movement or object slippage. Feedback from the sensor can be used to initiate any desired, appropriate corrective response.

Other objects and features of the invention will become apparent from the following detailed description and drawing disclosing what are presently contemplated as being the best modes of the invention.

THE DRAWING

In the drawing:

FIG. 1 is a perspective view of a typical transducer as used in the invention;

FIG. 2, a greatly enlarged sectional view through a sensor of the invention, with arrows showing typical reflected signals; and FIG. 3, a typical electrode arrangement for a sensor of the invention.

DETAILED DESCRIPTION OF THE DRAWINGS

Figure 1:
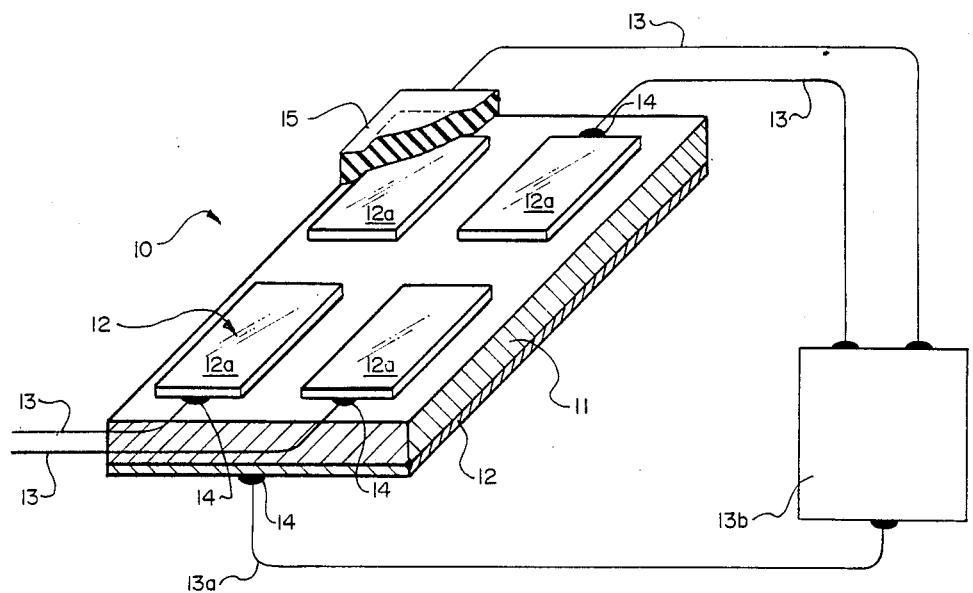

Referring now to the drawing:

In the illustrated, preferred embodiment, a typical four-element sensor array of the invention is shown generally at 10. In this embodiment a transducer, comprising a thin film sheet of polyvinylidene fluoride (PVDF) 11, has extremely thin sheets of aluminum-tin foil 12 on opposite surfaces thereof. Individual sensing elements 12a and arrays in any desired pattern arrangement are constructed by removing, as by etching away, portions of one or both of the metal sheets 12 to provide an appropriate pattern on the transducer material 11. Alternatively, the desired pattern can be deposited by vacuum deposit technique or other known methods. Electrical lead wires 13 and 13a are respectively electrically bonded at 14 to the remaining metal electrodes 12a and the other metal sheet 12, and are electrically connected to a suitable circuit 13b.

An elastomeric sheet of deformable, resilient material 15, having well-known mechanical and speed of sound characteristics, is placed over the sensor electrodes 12a. The object to be contacted by sensor array 10 deforms the exposed surface of the elastomeric sheet.

Figure 2:
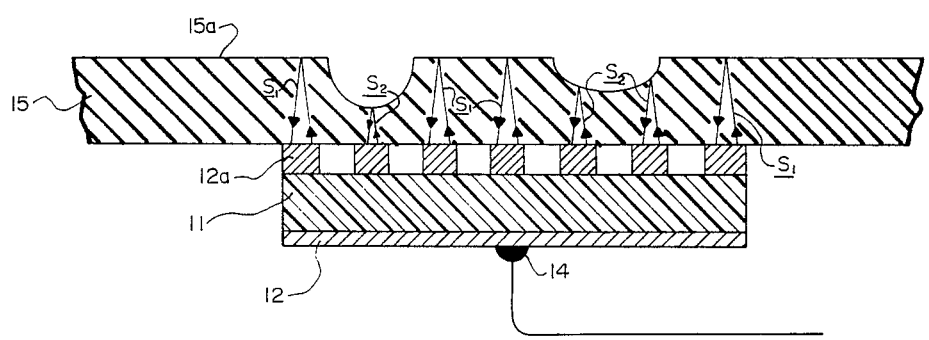

As shown in FIG. 2, the elements 12a, which serve as electrodes, excite the PVDF 11 to transmit signals S through the elastomer 15 that are reflected by (1) air, and (2) any object that is pressed against the elastomer 15 back to the sensing elements 12a. Conventional circuitry can measure the echo time from each individual electrode 12a, or can average the echo response times from several electrodes, depending upon the specific application.

In addition, the echo polarity, as determined by the acoustic impedance of a contacted object with respect to the impedance of the sheet 15 can be determined using conventional electrical circuits. With differing polarity sensing, the force sensor 10 can be readily calibrated to differentiate, for example, between metal, plastic, fabric or other materials, as necessary to the particular use of the invention. Such echo polarity determination can take place without any appreciable deformation of the elastomer 15, thereby greatly increasing the sensitivity and consequently the usefulness of the sensor.

Various arrangements of electrode patterns can be used in practicing the invention, depending upon the use to be made of the device and other governing criteria. The electrode pattern may be determined by the size of the sensor surface or the sensitivity desired as well as by the tasks to be performed by the sensor.

In the preferred embodiment of the invention, PVDF is used because of the low acoustic cross-coupling and its impedance match with elastomers. It is clear, however, that transducers made of other materials, such as ceramics, can be utilized should they prove advantageous under given circumstances.

Conventional pulse-echo circuitry or phase-shift circuitry may be used as circuitry 13b to determine the ultrasonic transit time, which is proportional to the thickness of the deformable medium used.

With the thickness determined at each transducer, a pattern of force (either direct or reactionary) applied to the face of the deformable member can be measured and sensing of a contacted or contacting object can be determined, as well as the shape of such object.

Figure 3:
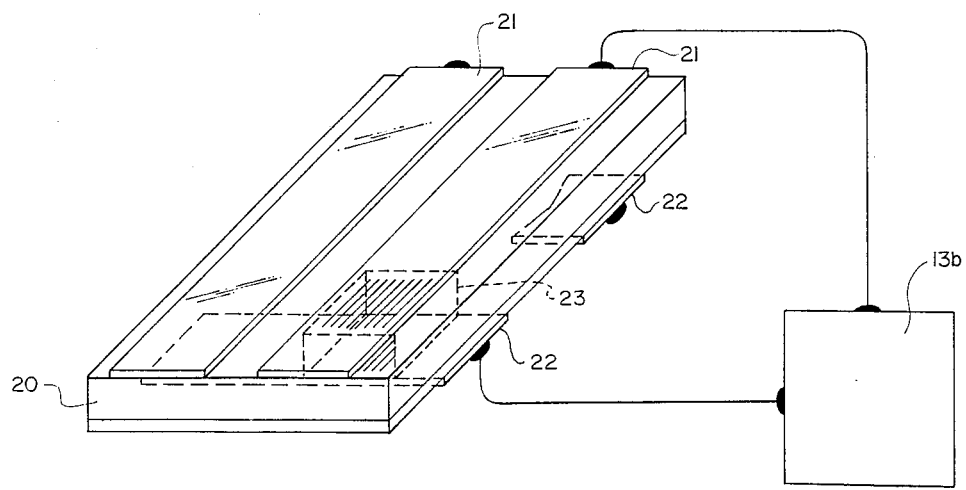

The transducers can be individually coupled into the circuit used, or a method of cross-point switching may be used. As shown best in FIG. 3, a PVDF transducer 20 has spaced parallel electrode strips 21 on one face thereof and spaced, parallel electrode strips 22 on the opposite face thereof. The strips 22 extend normal to the strips 21, and each strip 21 and each strip 22 are connected to electrical leads. If a particular strip 21 is switched on by the circuitry used at the same time a particular strip 22 is switched on, the volume of the PVDF between the strips indicated approximately by the dotted line box 23 in the embodiment shown, will be activated. Such an arrangement greatly reduces the number of electrical leads necessary for operation of a sensor having many transducers. If individual transducers are used, having their own wires, then for n rows and m columns of transducers, the number of leads required is n×m. However, with cross-point switching as described above, the number of leads required is only n+m.

It will be apparent that in addition to indicating contact of any portion of the surface of the deformable medium, and the areas of such contact, the sensor can measure force applied to such surface and the distribution of such force. Further, if x and y axes are established at the contact face of the deformable medium, torques applied about such axes can be readily measured.

Although a preferred form of our invention has been herein disclosed, it is to be understood that the present disclosure is by way of example and that variations are possible without departing from the subject matter coming within the scope of the following claims, which subject matter we regard as our invention.

I claim:

1. A sensor comprising
   a deformable medium;
   ultrasonic transducer means for transmitting an ultrasonic signal at one point into the said medium and for receiving an echo returned after said ultrasonic signal has been transmitted and returned from a surface of the medium opposite said one point; and current means for determining the time differential between transmission of the signal and the receipt of the echo and for converting said time differential into a distance measurement for determining deformation of the medium and for determining the echo polarity.

2. A sensor as in claim 1, wherein the deformable medium comprises a layer of resilient material.

3. A sensor as in claim 2, wherein the layer of resilient material is an elastomer.

4. A sensor as in claim 3, wherein the layer of resilient material is rubber.

5. A sensor as in claim 3, wherein the layer of resilient material is silicone rubber.

6. A sensor as in claim 3, wherein the layer of resilient material is natural rubber.

7. A sensor as in claim 3, wherein the layer of resilient material is synthetic rubber.

8. A sensor as in claim 1, wherein the ultrasonic transducer means comprises
a layer of polyvinylidene fluoride.

9. A sensor as in claim 2, wherein the ultrasonic transducer means comprises
a layer of polyvinylidene fluoride.

* * * * *